United States Patent
Daeuwel et al.

(10) Patent No.: US 8,263,370 B2
(45) Date of Patent: Sep. 11, 2012

(54) PROCESS FOR CONTINUOUSLY PREPARING URETHANE-CONTAINING (METH)ACRYLIC ESTERS

(75) Inventors: Juergen Daeuwel, Heidelberg (DE); Steffen Maurer, Dirmstein (DE); Rainer Stuermer, Roedersheim-Gronau (DE)

(73) Assignee: BASF SE, Ludwigshafen (DE)

( * ) Notice: Subject to any disclaimer, the term of this patent is extended or adjusted under 35 U.S.C. 154(b) by 205 days.

(21) Appl. No.: 12/778,426

(22) Filed: May 12, 2010

(65) Prior Publication Data
US 2010/0291641 A1   Nov. 18, 2010

Related U.S. Application Data

(60) Provisional application No. 61/177,292, filed on May 12, 2009.

(30) Foreign Application Priority Data

May 12, 2009 (DE) .................. 10 2009 003 036

(51) Int. Cl.
*C12P 13/00* (2006.01)
*C12P 7/62* (2006.01)

(52) U.S. Cl. ........ 435/128; 435/135; 435/196; 435/197; 435/198

(58) Field of Classification Search .................. 435/128, 435/135, 196, 197, 198
See application file for complete search history.

(56) References Cited

U.S. PATENT DOCUMENTS

| 4,820,830 | A | 4/1989 | Blank |
|---|---|---|---|
| 5,240,835 | A | 8/1993 | Pettrone et al. |
| 7,164,037 | B2 * | 1/2007 | Dietsche et al. ............... 560/132 |
| 2006/0286647 | A1 * | 12/2006 | Allard et al. .................. 435/134 |
| 2007/0197820 | A1 * | 8/2007 | Van Holen et al. ........... 560/158 |

FOREIGN PATENT DOCUMENTS

| DE | 10 2005 016 252 B3 | 2/2007 |
|---|---|---|
| EP | 0 136 813 A2 | 4/1985 |
| JP | 2001-40039 | 2/2001 |
| WO | WO 2004/050888 A1 | 6/2004 |

OTHER PUBLICATIONS

Levy, L. J. Polymer Sci., Part A: Polymer Chemistry (1992) 30: 569-576.*
Reis-Costa et al. Protein Peptide Lett. (2003) 10(6): 619-628.*
Machine translation of DE 102005016225 downloaded from the EPO May 7, 2012.*
Adam B. Hajjar et al., "Preparation of Monomeric Acrylic Ester Intermediates Using Lipase Catalysed Transesterifications in Organic Solvents", Biotechnology Letters, vol. 12, No. 11, 1990, pp. 825-830.
Regina Derango et al., "The Lipase-Catalyzed Synthesis of Carbamoyloxyethyl Methacrylate", Biotechnology Letters, vol. 16, No. 3, Mar. 1994, pp. 241-246.

* cited by examiner

*Primary Examiner* — Susan Hanley
(74) *Attorney, Agent, or Firm* — Oblon, Spivak, McClelland, Maier & Neustadt, L.L.P.

(57) ABSTRACT

A process for preparing urethane-containing (meth)acrylic esters (U) by reacting a urethane-containing alcohol (A) with a (meth)acrylic ester of a saturated alcohol (G) in the presence of at least one polymerization inhibitor (P) with an enzyme (E) as a catalyst in a reactor, wherein the (meth)acrylic ester of a saturated alcohol (G) and the urethane-containing alcohol (A) are passed continuously through at least one fixed bed reactor filled with an immobilized enzyme (E) as a catalyst.

13 Claims, No Drawings

PROCESS FOR CONTINUOUSLY PREPARING URETHANE-CONTAINING (METH)ACRYLIC ESTERS

The present invention relates to a process for continuously preparing urethane-containing (meth)acrylic esters The preparation of (meth)acrylic esters is accomplished usually by acid- or base-catalyzed esterification or transesterification of (meth)acrylic acid or other (meth)acrylic esters with alcohols at temperatures of 40 to significantly more than 100° C. Owing to the high temperatures, the addition of high amounts of polymerization inhibitors is required in order to suppress undesired polymerization of the monomers. This often gives rise to complex and sometimes colored product mixtures. To remove discoloration and unconverted reactants, the product mixtures are worked up by inefficient alkaline scrubbing. The scrubbing process is laborious and costly, since partly esterified products in particular can be extracted and removed only slowly.

The preparation of urethane-containing (meth)acrylates via a conventional acid-catalyzed esterification is additionally difficult, since urethane groups are acid-sensitive.

JP 2001-40039 A describes carbamate-containing (meth)acrylic esters which are prepared via an acid-catalyzed esterification. A disadvantage of the process described is that the purity of the product obtained is only 75.9% with a mass balance of 95%.

EP 136 813 A2 describes the two-stage preparation of N-substituted, carbamate-containing acrylates by reaction of polyhydroxyalkylated acrylates with isocyanates. A disadvantage of the process described is the restriction to those substrates which are available as isocyanates. For example, N,N-disubstituted carbamates are not preparable by this process, and likewise those with N-substituents which bear isocyanate-reactive groups. For the reaction with isocyanate, toxic tin compounds are additionally needed as a catalyst.

The preparation of (meth)acrylic esters by an enzymatic esterification or transesterification is known.

Hajjar et al. describe, in Biotechnol. Lett. 1990, 12, 825-830, the enzymatic transesterification of cyclic and open-chain alkanediols with ethyl acrylate with a lipase from *Chromobacterium viscosum*. The reactions proceed at an 18-fold molar excess of the alkyl acrylate over the diol in a solvent-free system. This gives rise to mixtures of mono- and diacrylates.

U.S. Pat. No. 5,240,835 describes the transesterification of alkyl acrylates with alcohols with catalysis by a biocatalyst from *Corynebacterium oxydans*. By way of example, the reaction of a 96-fold molar excess of ethyl acrylate with 2,2-dimethyl-1,3-propanediol is detailed there. Only 21% yield was obtained at 30° C. after 3 days.

Derango et al. describe, in Biotechnol. Lett. 1994, 16, 241-246, the lipase-catalyzed preparation of carbamoyloxyethyl methacrylate by transesterification of 2-hydroxyethyl carbamate with vinyl methacrylate. Complete conversion is achieved by virtue of the specific vinyl methacrylate reactant, since vinyl alcohol released is withdrawn from the reaction equilibrium as acetaldehyde. A disadvantage of this process is that vinyl methacrylate is not commercially available.

WO 2004/05088 A1 discloses a further enzyme-catalyzed preparation process for urethane-containing (meth)acrylic esters. A disadvantage of the process described is that the products have a relatively low purity and are nevertheless processed further in unpurified form.

A further disadvantage of the processes described is that the transesterification is effected batchwise, which is disadvantageous for a preparation of urethane-containing (meth)acrylic esters on a large scale.

It was therefore an object of the present invention to provide an alternative process with which urethane-containing (meth)acrylic esters are preparable continuously from single, economically obtainable reactants.

The object is achieved by a process for preparing urethane-containing (meth)acrylic esters (U) by reacting a urethane-containing alcohol (A) with a (meth)acrylic ester of a saturated alcohol (G) in the presence of at least one polymerization inhibitor (P) with an enzyme (E) as a catalyst in a reactor, wherein the (meth)acrylic ester of a saturated alcohol (G) and the urethane-containing alcohol (A) are passed continuously through at least one fixed bed reactor filled with an immobilized enzyme (E) as a catalyst.

With the aid of the process according to the invention, the preparation of urethane-containing (meth)acrylic esters is possible under mild conditions. Moreover, no significant polymer formation occurs. What is particularly advantageous about the process according to the invention is that the urethane-containing (meth)acrylic esters are obtained continuously by an enzymatic transesterification, which makes their preparation accessible on the industrial scale.

Urethane groups in the context of this document are O-substituted and N-unsubstituted, -monosubstituted or -disubstituted structural elements of the formula >N—C(=O)—O—.

(Meth)acrylic acid in this document represents methacrylic acid and acrylic acid, preferably acrylic acid.

"Saturated" in the context of this document means compounds without C—C multiple bonds (except, of course, the C=C double bond in the (meth)acryloyl units).

Urethane-containing alcohols (A) are those compounds which comprise at least one urethane group, preferably 1 to 10 urethane groups, more preferably 1 to 5 urethane groups, even more preferably 1 to 2 urethane groups and especially one urethane group, and at least one hydroxyl group (—OH), preferably 1 to 10 hydroxyl groups, more preferably 1 to 6 hydroxyl groups, even more preferably 1 to 3 hydroxyl groups, particularly 1 to 2 hydroxyl groups and especially one hydroxyl group.

Preferred urethane-containing alcohols (A) have an average molar mass of 105 to 800 000 g/mol, preferably to 25 000 g/mol, more preferably to 5000 and most preferably to 4500 g/mol.

Particularly preferred urethane-containing alcohols (A) are those which are obtainable by
a) reacting an amine with a carbonate and
b) optionally purifying the reaction mixture obtainable from a).

Suitable amines for this reaction are ammonia, primary or secondary amines; carbonates are O,O'-disubstituted carbonates with the —O—C(=O)—O— structural element.

Very particularly preferred urethane-containing alcohols (A) are those which are obtainable according to the following reaction equation:

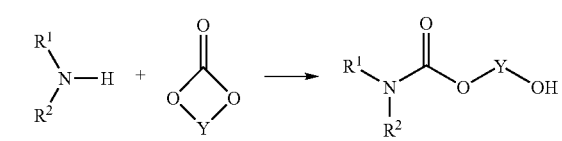

in which
R$^1$, R$^2$ are each independently hydrogen, C$_1$-C$_{18}$-alkyl, C$_2$-C$_{18}$-alkyl optionally interrupted by one or more oxygen and/or sulfur atoms and/or one or more substituted or unsubstituted imino groups, C$_2$-C$_{18}$-alkenyl, C$_6$-C$_{12}$-aryl, C$_5$-C$_{12}$-cycloalkyl or a five- or six-membered heterocycle having oxygen, nitrogen and/or sulfur atoms, where the radicals mentioned may each be substituted by aryl, alkyl, aryloxy, alkyloxy, heteroatoms and/or heterocycles, or a group of the formula —[X$_i$]$_k$—H, $X_i$ for each i=1 to k may independently be selected from the group of —CH$_2$—CH$_2$—O—, —CH$_2$—CH$_2$—N(H)—, —CH$_2$—CH$_2$—CH$_2$—N(H)—, —CH$_2$—CH(NH$_2$)—, —CH$_2$—CH(NHCHO)—, —CH$_2$—CH(CH$_3$)—O—, —CH(CH$_3$)—CH$_2$—O—, —CH$_2$—C(CH$_3$)$_2$—O—, —C(CH$_3$)$_2$—CH$_2$—O—, —CH$_2$—CH$_2$—CH$_2$—O—, —CH$_2$—CH$_2$—CH$_2$—CH$_2$—O—, —CH$_2$—CHVin-O—, —CHVin-CH$_2$—O—, —CH$_2$—CHPh-O— and —CHPh-CH$_2$—O—, in which Ph is phenyl and Vin is vinyl, k is from 1 to 50 and Y is C$_2$-C$_{20}$-alkylene or C$_2$-C$_{20}$-alkylene interrupted by one or more oxygen and/or sulfur atoms and/or one or more substituted or unsubstituted imino groups and/or by one or more —(CO)—, —O(CO)O—, —(NH)(CO)O—, —O(CO)(NH)—, —O(CO)— or —(CO)O groups, where the radicals mentioned may each be substituted by aryl, alkyl, aryloxy, alkyloxy, heteroatoms and/or heterocycles. $R^1$ and $R^2$ may also together form a ring.

$R^1$ and $R^2$ are preferably each independently hydrogen, C$_1$-C$_{12}$-alkyl, C$_5$-C$_6$-cycloalkyl or a group of the formula —[$X_i$]$_k$—H; $R^1$, and $R^2$ are more preferably each independently hydrogen, C$_1$-C$_4$-alkyl, C$_5$-C$_6$-cycloalkyl or a group of the formula —[$X_i$]$_k$—H, and even more preferably hydrogen, C$_1$-C$_4$-alkyl or a group of the formula —[$X_i$]$_k$—H. In particular, one of the $R^1$ and $R^2$ radicals is hydrogen and the other is C$_1$-C$_4$-alkyl, or a group of the formula —[$X_i$]$_k$—H.

Preferred $X_i$ are —CH$_2$—CH$_2$—O—, —CH$_2$—CH$_2$—N(H)—, —CH$_2$—CH$_2$—CH$_2$—N(H)—, —CH$_2$—CH(NH$_2$)—, —CH$_2$—CH(NHCHO)—, —CH$_2$—CH(CH$_3$)—O— und —CH(CH$_3$)—CH$_2$—O—, particular preference being given to —CH$_2$—CH$_2$—O—, —CH$_2$—CH$_2$—N(H)—, —CH$_2$—CH$_2$—CH$_2$—N(H)— and —CH$_2$—CH(NH$_2$)— very particular preference to —CH$_2$—CH$_2$—O—, —CH$_2$—CH$_2$—N(H)— and —CH$_2$—CH$_2$—CH$_2$—N(H)—.

k is preferably 1 to 30, more preferably 1 to 20, even more preferably 1 to 10 and especially 1 to 5.

Examples of $R^1$ and/or $R^2$ are hydrogen, methyl, ethyl, isopropyl, n-propyl, n-butyl, isobutyl, sec-butyl, tert-butyl, n-hexyl, n-heptyl, n-octyl, n-decyl, n-dodecyl, n-tetradecyl, n-hexadecyl, n-octadecyl, n-eicosyl, 2-ethylhexyl, cyclopentyl, cyclohexyl, cyclooctyl, cyclododecyl, 2-hydroxyethyl, 2-hydroxypropyl, 1-hydroxypropyl, 5-hydroxy-3-oxapentyl, 8-hydroxy-3,6-dioxaoctyl or 11-hydroxy-3,6,9-trioxaundecyl.

Y is preferably C$_2$-C$_{10}$-alkylene, more preferably C$_2$-C$_6$-alkylene, even more preferably C$_2$-C$_4$-alkylene, particularly C$_2$-C$_3$-alkylene and especially C$_2$-alkylene, where the radicals mentioned may each be substituted by aryl, alkyl, aryloxy, alkyloxy, heteroatoms and/or heterocycles.

Examples of Y are 1,2-ethylene, 1,2-propylene, 1,1-dimethyl-1,2-ethylene, 1-hydroxymethyl-1,2-ethylene, 2-hydroxy-1,3-propylene, 1,3-propylene, 1,4-butylene, 1,6-hexylene, 2-methyl-1,3-propylene, 2-ethyl-1,3-propylene, 2,2-dimethyl-1,3-propylene and 2,2-dimethyl-1,4-butylene, preference being given to 1,2-ethylene, 1,2-propylene, 1,3-propylene, particular preference to 1,2-ethylene and 1,2-propylene and very particular preference to 1,2-ethylene.

Examples of amines include ammonia, methylamine, dimethylamine, ethylamine, diethylamine, isopropylamine, diisopropylamine, n-butylamine, di-n-butylamine, tert-butylamine, monoethanolamine, diethanolamine, propanolamine, dipropanolamine, piperidine, piperazine, pyrrolidine, cyclopentylamine, cyclohexylamine, aniline, ethylenediamine, diethylenetriamine, triethylenetetramine, tetraethylenepentamine and polymers with amine functions, as described in WO 04/050888 A1 at page 5 from line 28 to page 6 line 33.

Examples of carbonates include ethylene carbonate, 1,3-propylene carbonate and 1,2-propylene carbonate.

Preferred urethane-containing alcohols (A) are those compounds as disclosed in German published specification DE 10 2005 016 225 A1. Among the binary mixtures of structurally isomeric β-hydroxyalkyl carbamates specified therein, the isomer mixture of hydroxypropyl carbamate in particular is preferred for the process according to the invention. Hydroxypropyl carbamate is obtained by reaction of 1,2-propylene carbonate with ammonia according to DE 10 2005 016 255 A1.

The reaction of the amine with the carbonate is known per se, for example from U.S. Pat. No. 4,820,830 B, column 4 line 44 to column 5 line 9, and is not restricted.

Typically, the amine and the carbonate are reacted with one another in a stoichiometry of 0.7 to 1.2 mol of amine : 1 mol of carbonate, preferably 0.8-1.2:1, more preferably 0.9-1.1:1, even more preferably 0.95-1.1:1 and especially 1:1 mol/mol. The reaction is effected generally at a temperature of 0 to 120° C., particularly at 20 to 100° C., even more preferably 30 to 80° C. and even more preferably 40 to 80° C. The reaction has generally ended within 12 hours, preferably within 15 minutes to 10 hours, more preferably within 30 minutes to 8 hours, even more preferably 45 minutes to 6 hours and especially within 1 to 4 hours.

The total amine number to DIN 53176 of the urethane-containing alcohol (A) should not be more than 200 mg KOH/g preferably not more than 100 and most preferably not more than 80 mg KOH/g.

The reaction of the amine with the carbonate can be performed without solvent or in the presence of one, for example alcohols, ethers, ketones, hydrocarbons or water, preferably without solvent.

The urethane-containing alcohol (A) can be purified if desired in a further step, for example by filtration, distillation, rectification, chromatography, treatment with ionic exchangers, adsorbents, neutral, acidic and/or alkaline scrubbing, stripping or crystallization.

In the process according to the invention, the urethane-containing alcohol (A) can be used in purified form. To this end, the urethane-containing alcohol (A) is removed from low- and high-boiling secondary components continuously by a purifying distillation. The lower-boiling components are, for example, unconverted carbonate or the corresponding diols. Useful high boilers include relatively high molecular weight secondary components which are responsible for the coloring. The purifying distillation is effected continuously in the fine vacuum range, i.e. at a reduced pressure of 1 to 100 mbar, preferably 1 to 50 mbar, more preferably 1 to 20 mbar and especially in the range from 1 to 10 mbar. The temperature in the purifying distillation is typically in the range from 50 to 200° C., preferably in the range from 75 to 180° C. and more preferably in the range from 100 to 160° C. Owing to the short residence times and the relatively low thermal stress, compared to the batchwise distillation, a high-purity urethane-containing alcohol (A) is achievable.

(Meth)acrylic esters of a saturated alcohol (G) are preferably those esters of (meth)acrylic acid with a saturated C$_1$-C$_{10}$-alcohol.

Examples of compounds (G) are methyl (meth)acrylate, ethyl (meth)acrylate, n-butyl (meth)acrylate, isobutyl (meth)acrylate, n-octyl (meth)acrylate, 2-ethylhexyl (meth)acrylate, 1,2-ethylene glycol di- and mono(meth)acrylate, 1,4-butanediol di- and mono(meth)acrylate, 1,6-hexanediol diand mono(meth)acrylate, trimethylolpropane tri(meth)acrylate and pentaerythrityl tetra(meth)acrylate.

Particular preference is given to methyl (meth)acrylate, ethyl (meth)acrylate, n-butyl (meth)acrylate and 2-ethylhexyl (meth)acrylate, and very particular preference to methyl (meth)acrylate, ethyl (meth)acrylate and n-butyl (meth)acrylate.

Enzymes (E) usable in accordance with the invention are, for example, selected from hydrolases, esterases (E.G. 3.1.-.-), lipases (E.C. 3.1.1.3), glycosylases (E.C. 3.2.-.-) and proteases (E.C. 3.4.-.-) in free form or in chemically or physically immobilized form on a support, preferably lipases, esterases or proteases. Particular preference is given to Novozym® 435 (lipase from *Candida antarctica* B) or lipase from *Aspergillus* sp., *Aspergillus niger* sp., *Mucor* sp., *Penicilium cyclopium* sp., *Geotricum candidum* sp., *Rhizopus javanicus, Burkholdena* sp., *Candida* sp., *Pseudomonas* sp., or porcine pancreas, very particular preference being given to lipase from *Candida antarctica* B or from *Burkholderia* sp.

In the process, it is essential to the invention that the transesterification of the (meth)acrylic ester of a saturated alcohol (G) with a urethane-containing alcohol (A) is effected continuously with an enzyme (E) as a catalyst, by passing the (meth)acrylic ester of a saturated alcohol (G) and the urethane-containing alcohol (A) continuously through at least one fixed bed reactor filled with an immobilized enzyme (E) as a catalyst.

The (meth)acrylic ester of the saturated alcohol (G) can be mixed with the urethane-containing alcohol (A) beforehand, and this reaction mixture is subsequently passed through the at least one fixed bed reactor filled with an immobilized enzyme (E). The reactants can also be passed over the immobilized enzyme (E) separately and simultaneously. Preference is given to first preparing a reaction mixture of (meth)acrylic ester (G) and urethane-containing alcohol (A), which is then passed over the immobilized enzyme (E).

The molar ratio of (meth)acrylic ester of a saturated alcohol (G) (based on the (meth)acryloyl units) to urethane-containing alcohol (A) (based on hydroxyl groups) may vary within a wide range, for example in a ratio of 100:1 to 1:1, preferably 50:1 to 1:1, more preferably 20:1 to 1:1 and most preferably 10:1 to 1:1.

The enzyme (E) in the process according to the invention is immobilized on a suitable support. There exist five conventional methods of immobilizing enzymes, specifically adsorption, covalent binding, membrane entrapment, gel encapsulation and crosslinking. It is possible to use different support materials, and the chemical interactions of the support surface with the enzyme must be adjusted such that no undesired side effects, for example inactivation, arise. Suitable solid supports are in principle various inorganic and organic materials; the latter may be of natural or synthetic origin. Inorganic supports usually have a high pressure stability, whereas organic supports exhibit good chemical stability. The inorganic supports used are predominantly porous materials based on silicon oxides or aluminum oxides or mixtures thereof. Natural organic supports are, for example, polysaccharides, for example cellulose, starch, dextran, agarose and chitin. However, proteins such as collagen, gelatin and albumin are also employed. The synthetic organic polymers used are poly(meth)acrylates, polyacrylamides, vinyl and allyl polymers, polyesters or polyamides.

In the process according to the invention, preference is given to using enzymes which are already immobilized on a suitable support. Such immobilized enzymes, preferably lipases, are obtainable under the trade name Novozym® 435 (lipase from *Candida antarctica* B) from Novozymes.

The immobilized enzyme is provided in an apparatus suitable as a fixed bed reactor, for example a tube or a column. Subsequently, the reactants or preferably the premixed reaction mixture of a (meth)acrylic ester (G) and a urethane-containing alcohol (A) is/are pumped with the aid of a pump through the fixed bed reactor charged with the immobilized enzyme.

The enzymatic transesterification with a (meth)acrylic ester of a saturated alcohol (G) is effected generally at 0 to 100° C., preferably 20 to 80° C., more preferably 20 to 70° C., most preferably 20 to 60° C.

The reaction may proceed in organic solvents or mixtures thereof or without addition of solvents. The mixtures are generally substantially anhydrous (i.e. addition of water less than 10, preferably less than 5, more preferably less than 1% by volume).

The proportion of organic solvents is, for example, 0.01-30% by weight, preferably 0.1-5% by weight. Suitable organic solvents are those known for these purposes, for example tertiary monools such as $C_3$-$C_6$-alcohols, preferably tert-butanol, tert-amyl alcohol, pyridine, poly-$C_1$-$C_4$-alkylene glycol di-$C_1$-$C_4$-alkyl ethers, preferably polyethylene glycol di-$C_1$-$C_4$-alkyl ethers, for example 1,2-dimethoxyethane, diethylene glycol dimethyl ether, polyethylene glycol dimethyl ether 500, $C_1$-$C_4$-alkylene carbonates, especially propylene carbonate, $C_3$-$C_6$-alkyl acetates, especially tert-butyl acetate, THF, toluene, 1,3-dioxolane, acetone, isobutyl methyl ketone, ethyl methyl ketone, 1,4-dioxane, tert-butyl methyl ether, cyclohexane, methylcyclohexane, toluene, hexane, dimethoxymethane, 1,1-dimethoxyethane, acetonitrile, and the mono- or polyphasic mixtures thereof.

Optionally, aqueous solvents can be added to the organic solvents, such that—according to the organic solvent—mono- or polyphasic reaction solutions arise. Examples of aqueous solvents are water and aqueous, diluted (e.g. 10 to 100 mM) buffers, for example with a pH in the range from 6 to 8, for example potassium phosphate or TRIS-HCl buffer.

The water content in the reaction mixture is generally 0-10% by volume. Preference is given to using the reactants without pretreatment (drying, water doping).

Preference is given to performing the enzymatic transesterification without addition of water and organic solvents.

According to the invention, the reaction is performed continuously over at least one fixed bed reactor filled with an immobilized enzyme (E). To this end, the reactants or the premixed reaction mixture is/are pumped from a receiver vessel with the aid of a pump through the fixed bed reactor charged with the immobilized enzyme. The resulting crude product comprising the urethane-containing (meth)acrylic ester (U) is collected in a suitable reservoir vessel.

In a preferred embodiment of the process according to the invention, the crude product is first purified by distillation, in which case the azeotrope of saturated alcohol released and excess corresponding (meth)acrylic ester (G) and any entraining agent used is removed by means of an attached distillation column.

It is optionally possible to additionally use an entraining agent which forms an azeotrope with the saturated alcohol released and the corresponding (meth)acrylic ester (G) which is thus in excess. The entraining agent is preferably one whose azeotrope formed with the saturated alcohol released and the corresponding (meth)acrylic ester (G) which is thus in excess exhibits phase separation or which can be broken by addition of water. Suitable entraining agents of this kind are, for example, n-pentane, n-hexane, n-heptane, cyclohexane, methylcyclohexane, benzene, toluene, xylene and any desired mixtures thereof.

The distillation column used for the removal of the azeotrope is of a design known per se and has the customary internals. Useful column internals include in principle all common internals, for example trays, structured packings and/or random packings. Among the trays, preference is given to bubble-cap trays, sieve trays, valve trays, Thormann trays and/or dual-flow trays; among the random packings, preference is given to those comprising rings, helices, saddles or braids. In general, 5 to 20 theoretical plates are sufficient.

The azeotrope distilled off is subsequently condensed in a condenser of conventional design.

The product comprising the urethane-containing (meth)acrylic ester (U) which is purified in this way is subsequently fed to the second fixed bed reactor charged with immobilized enzyme (E) and pumped with the aid of a pump through this fixed bed reactor. The end product is collected in an attached reservoir vessel.

The power of the pump with which the reaction mixture is pumped through the fixed bed reactors charged with immobilized enzyme is adjusted such that the thermodynamic equilibrium state is achieved at the outlet of the enzyme fixed bed.

Optionally, it is possible in another embodiment of the process according to the invention that the urethane-containing (meth)acrylic ester, after leaving the at least one fixed bed reactor charged with immobilized enzyme (E) and before being collected in the reservoir vessel, is subjected to an extraction operation.

The extraction is effected typically with water, in which case the residual urethane-containing alcohol (A) is transferred into the aqueous phase and is thus removed from the end product. The organic phase comprising urethane-containing (meth)acrylic ester (U) and any residual (meth)acrylic ester (G) can be purified in an above-described distillation column, in which case the (meth)acrylic ester (G) is removed from the end product as a low boiler.

If solvents are used, the removal from the organic solvent is generally effected by distillation, rectification, or in the case of solid reaction products by filtration.

For further purification of the reaction product, it is also possible to perform chromatography or a distillative purification.

If a distillative purification to purify the reaction product is performed, the urethane-containing (meth)acrylic ester (U) is isolated as the top product in a further distillation step from the bottoms obtained in the optional solvent distillation, and stabilized with at least one of the polymerization inhibitors specified below. Among the stabilizers mentioned there, especially hydroquinone monomethyl ether and phenothiazine are suitable for the distillative purification.

The rectification column usable for this distillation step is of known design, for example columns with random packing, columns with structured packing or tray columns, and has separating internals (for example bubble-cap trays, sieve trays or dual-flow trays), or comprises random packings or structured packings. The customary internals preferably have 10 to 20 theoretical plates. Thin-film evaporators are also an option. Evaporators and condensers are likewise of conventional design.

The urerthane-containing (meth)acrylic ester (U) is preferably obtained at a bottom temperature of 100-140° C., preferably of 110-130° C., and a top pressure of 1 to 100 mbar, preferably of 1 to 50 mbar, more preferably of 1 to 10 mbar and especially of 1 to 5 mbar.

For stabilization, a solution of 0.05-0.5% hydroquinone monomethyl ether or another similarly effective storage stabilizer can be sprayed into the condenser, the amount being selected such that the condensate has a storage stabilizer concentration of 10-20 ppm. A portion of the condensate, preferably 10-20%, can be fed back to the column as a return stream.

The urethane-containing (meth)acrylic ester (U) obtained has, according to gas chromatography analysis, a purity of at least 98.5%, preferably at least 99.0% and more preferably at least 99.5%.

The bottom product of the distillative purification, which consists principally of residual urethane-containing (meth)acrylic ester (U), Michael addition products, stabilizer and polymers, can be passed into a residue distillation and/or residue cleavage.

It will be appreciated that it is also possible to combine the distillation units of the optional solvent distillation and the distillative purification. In this case, the pure urethane-containing (meth)acrylic ester (U) can be discharged via a side draw, preferably in gaseous form, in the lower column region, preferably in the lower half, more preferably in the lower third, condensed and stabilized as described above.

In the purification step, however, preference is given to removing only the enzyme used and any solvent used.

The reaction conditions in the enzymatic transesterification are mild. The low temperatures and otherwise mild conditions prevent the formation of by-products in the transesterification, which can otherwise originate, for example, from chemical catalysts or result from undesired free-radical polymerization of the (meth)acrylic ester (G) used, which can otherwise be prevented only by addition of stabilizers.

Since the (meth)acrylic ester of a saturated alcohol (G) used in the process according to the invention and the urethane-containing (meth)acrylic ester (U) are both polymerizable compounds, sufficient inhibition of polymerization has to be ensured in all process steps. Therefore, the transesterification, in accordance with the invention, takes place in the presence of at least one polymerization inhibitor (P). This may be the storage stabilizer present in any case in the (meth)acrylic ester (G), but it is also possible to add a further polymerization inhibitor.

In general, based on the unsaturated monomers, per individual substance, from 1 to 10 000 ppm, preferably from 10 to 5000 ppm, more preferably from 30 to 2500 ppm and especially from 50 to 1500 ppm of a suitable polymerization inhibitor (P) is used.

Suitable polymerization inhibitors (P) may, for example, be N-oxides (nitroxyl or N-oxyl radicals, i.e. compounds which have at least one >N—O— group), for example 4-hydroxy-2,2,6,6-tetramethylpiperidine N-oxyl, 4-oxo-2,2,6,6-tetramethylpiperidine N-oxyl, 4-acetoxy-2,2,6,6-tetramethylpiperidine N-oxyl, 2,2,6,6-tetramethylpiperidine N-oxyl, 4,4',4''-tris(2,2,6,6-tetramethylpiperidine N-oxyl) phosphite or 3-oxo-2,2,5,5-tetramethylpyrrolidine N-oxyl; mono- or polyhydric phenols which may have one or more alkyl groups, for example alkylphenols, for example o-, m- or p-cresol (methylphenol), 2-tert-butylphenol, 4-tert-butylphenol, 2,4-di-tert-butylphenol, 2-methyl-4-tert-butylphenol, 2-tert-butyl-4-methylphenol, 2,6-tert-butyl-4-methylphenol, 4-tert-butyl-2,6-dimethylphenol or 6-tert-butyl-2,4-dimethylphenol; quinones, for example hydroquinone, hydroquinone monomethyl ether, 2-methylhydroquinone or 2,5-di-tert-butylhydroquinone; hydroxyphenols, for example pyrocatechol (1,2-dihydroxybenzene) or benzoquinone; aminophenols, for example p-aminophenol; nitrosophenols, for example p-nitrosophenol; alkoxyphenols, for example 2-methoxyphenol (guaiacol, pyrocatechol monomethyl ether), 2-ethoxyphenol, 2-isopropoxyphenol, 4-methoxyphenol (hydroquinone monomethyl ether), mono- or di-tert-butyl-4-methoxyphenol; tocopherols, for example α-tocopherol and 2,3-dihydro-2,2-dimethyl-7-hydroxybenzofuran (2,2-dimethyl-7-hydroxycoumaran), aromatic amines, for example N,N-diphenylamine or N-nitrosodiphenylamine; phenylenediamines, for example N,N'-dialkyl-p-phenylenediamine, where the alkyl radicals may be the same or different and each consist independently of from 1 to 4 carbon atoms and may be straight-chain or branched, for example N,N'- dimethyl-p-phenylenediamine or N,N'-diethyl-p-phenylenediamine, hydroxylamines, for example N,N-diethylhydroxylamine, imines, for example methyl ethyl imine or methylene violet, sulfonamides, for example N-methyl-4-toluenesulfonamide or N-tert-butyl-4-toluenesulfonamide, oximes, such as aldoximes, ketoximes or amide oximes, for example diethyl ketoxime, methyl ethyl ketoxime or salicylaldoxime, phosphorus compounds, for example triphenylphosphine, triphenyl phosphite, triethyl phosphite, hypophosphorous acid or alkyl esters of phosphorous acids; sulfur compounds, for example diphenyl sulfide or phenothiazine; metal salts such as copper or manganese, cerium, nickel, chromium salts, for example chlorides, sulfates, salicylates, tosylates, acrylates or acetates, for example copper acetate, copper(II) chloride, copper salicylate, cerium(III) acetate or cerium(III) ethylhexanoate, or mixtures thereof.

The polymerization inhibitor (mixture) used is preferably at least one compound from the group of hydroquinone, hydroquinone monomethyl ether, phenothiazine, 4-hydroxy-2,2,6,6-tetramethylpiperidine N-oxyl, 4-oxo-2,2,6,6-tetramethylpiperidine N-oxyl, 2-tert-butylphenol, 4-tert-butylphenol, 2,4-di-tert-butylphenol, 2-tert-butyl-4-methylphenol, 6-tert-butyl-2,4-dimethylphenol, 2,6-di-tert-butyl-4-methylphenol, 2-methyl-4-tert-butylphenol, hypophosphorous acid, copper acetate, copper(II) chloride, copper salicylate and cerium(III) acetate.

Very particular preference is given to using phenothiazine and/or hydroquinone monomethyl ether (MEHQ) as the polymerization inhibitor (P).

To further promote the stabilization, an oxygenous gas will preferably be present, preferably air or a mixture of air and nitrogen (lean air).

In a preferred embodiment, the process according to the invention makes it possible to obtain urethane-containing (meth)acrylic esters (U) of the formula (I)

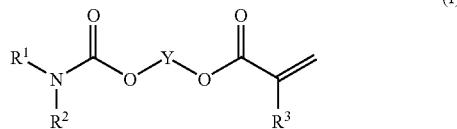

(I)

in which
$R^1$ and $R^2$ are each as defined above,
Y is selected from 1,2-ethylene, 1,2-propylene, 1,1-dimethyl-1,2-ethylene, 1-hydroxymethyl-1,2-ethylene, 2-hydroxy-1,3-propylene, 2-hydroxy-1,3-propylene, 1,3-propylene, 1,4-butylene, 1,6-hexylene, 2-methyl-1,3-propylene, 2-ethyl-1,3-propylene, 2,2-dimethyl-1,3-propylene and 2,2-dimethyl-1,4-butylene,
$R^3$ is hydrogen or methyl, preferably hydrogen,
with the proviso that at least one of the $R^1$ and $R^2$ radicals is not hydrogen.

The urethane-containing (meth)acrylic esters (U) obtainable can advantageously be used as comonomers in poly(meth)acrylates or as reactive diluents in radiation-curable and/or dual-curable poly(meth)acrylates. Such poly(meth)acrylates are suitable as binders in radiation-curable or dual-curable coating materials. Coatings thus obtainable have very high scratch resistances, hardnesses, chemical stabilities, elasticity and adhesion, both on hydrophilic and on hydrophobic substrates.

A further use of the urethane-containing (meth)acrylic esters (U) prepared by the process according to the invention is as an additive in coating formulations. The urethane-containing (meth)acrylic esters (U) may be used either in basecoats or in topcoats. Owing to their exceptional properties, such as the increase in the scratch resistance and elasticity, and the lowering of the viscosity, especially in the case of branched polyacrylates, of a radiation-cured clearcoat, their use in topcoats is preferred.

For such a use, the urethane-containing (meth)acrylic ester (U) can suitably be blended with an addition of solvent in order to prevent the solid state and to keep the urethane-containing (meth)acrylic ester (U) in the liquid phase. Suitable solvents for this purpose are lower hydrocarbons miscible therewith, such as methanol, ethanol, propanol, isopropanol, butanol, hexanol and any desired mixtures thereof. Typically 0 to 40% by weight, preferably 5 to 30% by weight and more preferably 10 to 20% by weight of a suitable solvent are used, based in each case on the total weight of solvent and urethane-containing (meth)acrylic ester (U).

The examples which follow are intended to illustrate the properties of the invention, but without restricting them.

Unless stated otherwise, percent always means percent by weight and parts always mean parts by weight.

EXAMPLES

Example 1

Preparation of Hydroxypropyl Carbamate Acrylate

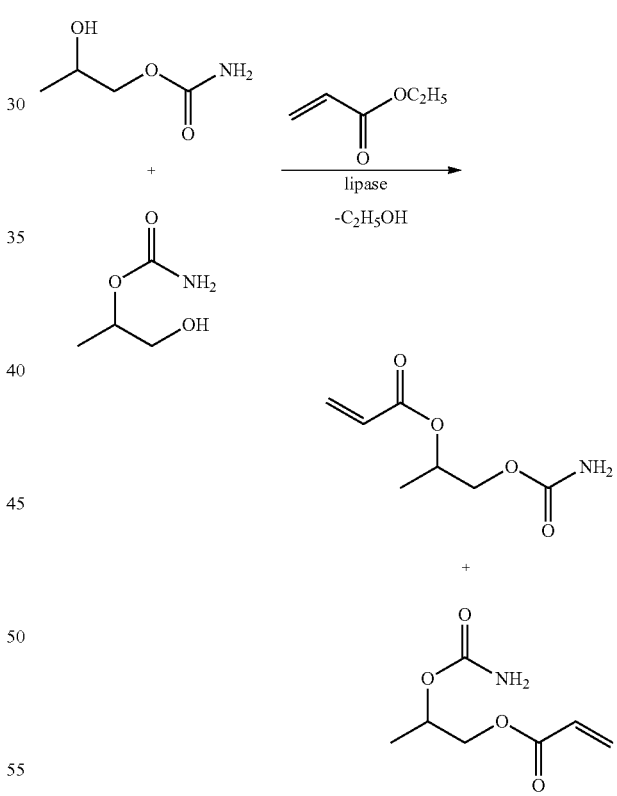

In a distillation apparatus, 1000 g of hydroxypropyl carbamate (isomer mixture) were first admixed with 600 ml of methanol, and then the methanol was distilled off at 50° C. under atmospheric pressure. Another 600 g of methanol were added and distilled off. Subsequently, the vacuum was adjusted to 3 mbar and the remaining solvent was removed by distillation at 60° C. for 30 minutes.

In a receiver vessel with attached jacketed glass column, pump and downstream 5 l reservoir vessel, the transesterification of ethyl acrylate with hydroxypropyl carbamate was carried out. The jacketed glass column (length 40 cm, diameter 1.35 cm) was charged with 14 ml of lipase (Novozym® 435). Then 2002.4 g (20.0 mol) of ethyl acrylate and 248.9 g (2.0 mol) of the hydroxypropyl carbamate which had been purified beforehand were mixed with one another in the receiver vessel. For stabilization, 400.5 mg (200 ppm, based on ethyl acrylate) of hydroquinone monomethyl ether were added. The temperature was adjusted to 40° C. Subsequently, with the aid of the pump, at a rate of 11 ml per hour, the initially charged reaction mixture was pumped through the jacketed glass column charged with enzyme and collected in the reservoir vessel.

After 3 h 38 min, the output in the reservoir vessel was 21.5 g. The conversion was 73.6%. Subsequently, the resulting crude product was analyzed by means of GC; it comprised 53.9% hydroxypropyl carbamate acrylate.

Example 2

Preparation of Hydroxypropyl Carbamate Acrylate—Extended Test

Example 1 was repeated, except that the pump was operated at a rate of 15 ml/h. The reaction time was a total of approx. 310 h, and the output in the reservoir vessel, the conversion and the purity were determined by means of GC analysis after various time intervals. The results are compiled in table 1.

TABLE 1

| Time [h:min] | Output [g] | Conversion [%] | Purity [%] |
|---|---|---|---|
| 0:00 | 0 | 0 | 0 |
| 3:13 | 46.4 | 58.2 | 43.2 |
| 5:04 | 83.1 | 58.0 | 43.1 |
| 21:09 | 307.9 | 63.0 | 48.4 |
| 26:59 | 384.9 | 62.7 | 49.7 |
| 46:03 | 650.8 | 61.8 | 46.5 |
| 52:10 | 733.4 | 60.9 | 47.4 |
| 74:30 | 1048.0 | 60.2 | 46.8 |
| 141:56 | 1982.4 | 55.6 | 44.1 |
| 164:26 | 2305.5 | 52.9 | 42.1 |
| 189:31 | 2660.5 | 55.2 | 44.8 |
| 191:36 | 2688.3 | not determined | 35.4 |
| 308:56 | 4349.3 | 43.9 | 52.9 |

It is evident that the performance optimum of the enzymatic fixed bed catalyst is at approx. 1 day, both with regard to the conversion and to the purity of the crude product.

Example 3

Preparation of Hydroxypropyl Carbamate Acrylate—Extended Test with 2nd Enzyme Column 250 g (comprising 0.9 mol of hydroxypropyl carbamate) were taken from the output from example 2 with a purity of 52.9%, and admixed with 2010 g (20.08 mol) of ethyl acrylate. At a temperature of 40° C., this mixture was conducted through a second jacketed glass column (length 40 cm, diameter 1.35 cm) charged with 12 ml of lipase (Novozym® 435) with the aid of a pump at a rate of 15 ml/h. The total reaction time was approx. 160 h, and the output in the reservoir vessel, the conversion and the purity were determined by means of GC analysis after various time intervals. The results are compiled in table 2.

TABLE 2

| Time [h:min] | Output [g] | Conversion [%] | Purity [%] |
|---|---|---|---|
| 0:00 | 0 | 0 | 0 |
| 16:40 | 233.1 | 75.7 | 73.1 |
| 23:56 | 331.3 | 74.6 | 71.4 |
| 42:41 | 594.4 | 75.0 | 72.7 |
| 64:46 | 924.2 | 73.7 | 71.3 |
| 89:21 | 1265.5 | 72.3 | 69.8 |
| 161:23 | 2256.0 | 68.3 | 65.6 |

It becomes clear that a second enzymatic fixed bed catalyst leads to significantly higher purities of the crude product. The performance optimum is likewise at approx. 1 day, both in relation to the conversion and to the purity of the crude product.

After the reaction had ended, the entire output was collected in a 2.5 l Miniplant vessel. According to GC analysis, the crude product comprised 70.2% hydroxypropyl carbamate acrylate. The crude product was subsequently washed with 491 g of deionized water. This gave 503.4 g of aqueous phase and an organic phase which, according to GC analysis, comprised 87.7% hydroxypropyl carbamate acrylate.

This organic phase was washed once again with 491 g f deionized water. This gave 546.9 g of aqueous phase and an organic phase which comprised 93.7% hydroxypropyl carbamate acrylate (GC analysis).

This organic phase was subsequently concentrated. 148.9 g of output were obtained; the product had a purity of 93.8% (GC analysis).

Example 4

Preparation of Hydroxypropyl Carbamate Acrylate

Example 1 was repeated, except that the reaction temperature was adjusted to 60° C. The pump was operated at a rate of 15 ml/h.

After 16 h 57 min, the output in the reservoir vessel was 241.1 g. The conversion was 71.0%. Subsequently, the resulting crude product was analyzed by means of GC; it comprised 68.2% hydroxypropyl carbamate acrylate.

After a total of 23 h 19 min, the reaction was ended. The output in the reservoir vessel was 328.4 g of crude product; this comprised, according to GC analysis, 67.5% hydroxypropyl carbamate acrylate.

The invention claimed is:

1. A process for preparing urethane-containing (meth)acrylic esters (U) comprising reacting a urethane-containing alcohol (A) with a (meth)acrylic ester of a saturated alcohol (G) in the presence of at least one polymerization inhibitor (P) with an enzyme (E) as a catalyst in a reactor, which comprises passing the (meth)acrylic ester of a saturated alcohol (G) and the urethane-containing alcohol (A) continuously through at least one fixed bed reactor filled with an immobilized enzyme (E) as a catalyst to form a urethane-containing (meth)acrylic ester, and extracting said urethane-containing (meth)acrylic ester with water.

2. The process according to claim 1, wherein the urethane-containing alcohol (A) is obtainable by the following reaction:

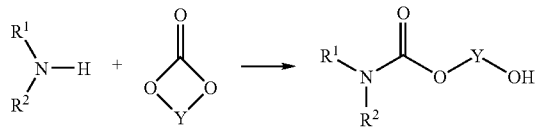

in which
R$^1$, R$^2$ are each independently hydrogen, C$_1$-C$_{18}$-alkyl, C$_2$-C$_{18}$-alkyl optionally interrupted by one or more oxygen and/or sulfur atoms and/or one or more substituted or unsubstituted imino groups, C$_2$-C$_{18}$-alkenyl, C$_6$-C$_{12}$-aryl, C$_5$-C$_{12}$-cycloalkyl or a five- or six-membered heterocycle having oxygen, nitrogen and/or sulfur atoms, where the radicals mentioned may each be substituted by aryl, alkyl, aryloxy, alkyloxy, heteroatoms and/or heterocycles, or a group of the formula —[X$_i$]$_k$—H,
X$_i$ for each i=1 to k may independently be selected from the group of —CH$_2$—CH$_2$—O—, —CH$_2$—CH$_2$—N(H)—, —CH$_2$—CH$_2$—CH$_2$—N(H)—, —CH$_2$—CH(NH$_2$)—, —CH$_2$—CH(NHCHO)—, —CH$_2$—CH(CH$_3$)—O—, —CH(CH$_3$)—CH$_2$O—, CH$_2$—C(CH$_3$)$_2$—O, —C(CH$_3$)$_2$—CH$_2$—O—, —CH$_2$—CH$_2$—CH$_2$—O—, —CH$_2$—CH$_2$—CH$_2$—CH$_2$—O—, —CH$_2$—CHVin-O—, —CHVin-CH$_2$—O—, —CH$_2$—CHPh-O— and —CHPh-CH$_2$—O—, in which Ph is phenyl and Vin is vinyl,
k is from 1 to 50 and
Y is C$_2$-C$_{20}$-alkylene or C$_2$-C$_{20}$-alkylene interrupted by one or more oxygen and/or sulfur atoms and/or one or more substituted or unsubstituted imino groups and/or by one or more —(CO)—, —O(CO)O—, —(NH)(CO)O—, —O(CO)(NH)—, —O(CO)— or —(CO)O groups, where the radicals mentioned may each be substituted by aryl, alkyl, aryloxy, alkyloxy, heteroatoms and/or heterocycles.

3. The process according to claim 2, wherein R$^1$ and R$^2$ are each independently hydrogen, C$_1$-C$_{12}$-alkyl, C$_5$-C$_6$-cycloalkyl or a group of the formula —[X$_i$]$_k$—H.

4. The process according to claim 2, wherein said amine and carbonate are reacted in a stoichiometry of 0.7 to 1.2 moles of amine: 1 mole of carbonate.

5. The process according to claim 2, wherein said a total amine number of said urethane-containing alcohol (A) is no more than 200 mg KOH/g.

6. The process according to claim 1, wherein the (meth)acrylic ester of a saturated alcohol is selected from the group of methyl (meth)acrylate, ethyl (meth)acrylate, n-butyl (meth)acrylate and 2-ethylhexyl (meth)acrylate.

7. The process according to claim 1, wherein the enzyme (E) is a lipase.

8. The process according to claim 1, wherein the (meth)acrylic ester of the saturated alcohol (G) is mixed with the urethane-containing alcohol (A) beforehand, and this reaction mixture is then passed over the at least one immobilized enzyme (E).

9. The process according to claim 1, wherein the molar ratio of (meth)acrylic ester of a saturated alcohol (G) to urethane-containing alcohol (A) is in the range from 50:1 to 1:1.

10. The process according to claim 1, further comprising purifying by distillation, the resultant extracted urethane-containing (meth)acrylic ester.

11. The process according to claim 1, wherein urethane-containing alcohol (A) is used in purified form, by removing the urethane-containing alcohol (A) from low- and high-boiling secondary components beforehand by a continuous purifying distillation.

12. The process according to claim 1, wherein said urethane-containing alcohol and said (meth)acrylic ester of a saturated alcohol are reacted at a temperature of 0 to 100° C.

13. The process according to claim 1, wherein said urethane-containing alcohol and said (meth)acrylic ester of a saturated alcohol are reacted at a temperature of 20 to 60° C.

* * * * *